United States Patent [19]
Chin et al.

[11] Patent Number: 5,585,327
[45] Date of Patent: Dec. 17, 1996

[54] 4-SUBSTITUTED PYRIDYL-3-CARBINOL COMPOSITIONS AND A CO-HERBICIDE

[75] Inventors: Hsiao-Ling Chin, Moraga; Yi-Qiu Wei, Pinole; Nhan H. Nguyen, Richmond; Michael P. Ensminger, Petaluma; Linda Willitts, Folsom; Derek P. Dagarin, Richmond, all of Calif.

[73] Assignee: Zeneca Limited, London, England

[21] Appl. No.: 236,300

[22] Filed: May 2, 1994

Related U.S. Application Data

[63] Continuation-in-part of Ser. No. 51,490, Apr. 22, 1993, Pat. No. 5,308,826.

[51] Int. Cl.$^6$ .......................... C07D 213/16; A01N 43/40
[52] U.S. Cl. ............................. 504/132; 504/130; 544/60; 544/124; 546/261; 546/286; 546/288; 546/290; 546/294; 546/296; 546/297; 546/301; 546/302; 546/304; 546/343; 546/266; 546/267; 546/283.4; 546/22
[58] Field of Search ............... 504/130,132; 544/60,124; 546/261,286, 288, 290, 294, 296, 297, 301, 302, 304, 343, 275, 266, 267, 283, 284, 283.4, 22

[56] References Cited

U.S. PATENT DOCUMENTS

| | | | |
|---|---|---|---|
| 4,116,665 | 9/1978 | Krumkalns | 504/66 |
| 4,407,806 | 10/1983 | Cherpeck | 546/399 |
| 5,055,476 | 10/1991 | Effland et al. | 514/335 |
| 5,308,826 | 5/1994 | Chin et al. | 504/132 |

FOREIGN PATENT DOCUMENTS

| | | | |
|---|---|---|---|
| 489670 | 6/1992 | European Pat. Off. | 504/66 |
| 1595261 | 8/1981 | United Kingdom | 504/66 |

OTHER PUBLICATIONS

Radinov et al., "Synthesis of 4-Amino-3-pyridinyl and 4-Amino-5-pyrimidinyl Aryl Ketones and Related Compounds via an *ortho* Lithiation Reaction", *Synthesis*, pp. 886-891, Nov. 1986.

Marsais et al., "Directed Lithiation of 4-Halopyridines: Chemo-selectivity, Regioselectivity and Application to Synthesis", *J. Het. Chem.*, 25, pp. 81-87, Jan.-Feb. 1988.

Chemical Abstracts, vol. 93, No. 21, Nov. 24, 1980, Abstract No. 199233b, E. V. Krumkalns, "Composition for Inhibiting the Growth of Injurious Aquatic Weeds".

*Primary Examiner*—Zinna Northington Davis
*Attorney, Agent, or Firm*—Marian T. Thomson; Joseph R. Snyder

[57] ABSTRACT

4-substituted pyridyl-3-carbinols of the formula

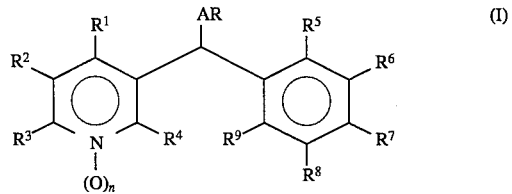

wherein R is hydrogen, or an acyl, alkyl or carbamyl group exhibit desirable preemergent and postemergent herbicidal activity. Also disclosed are herbicidal compositions comprising such compounds and methods of controlling undesirable vegetation employing such compounds. The compounds wherein AR is hydroxyl serve as useful intermediates for the production of the alpha-benzyl substituted compounds as well as exhibiting herbicidal activity.

13 Claims, No Drawings

4-SUBSTITUTED PYRIDYL-3-CARBINOL COMPOSITIONS AND A CO-HERBICIDE

This application is a continuation-in-part of U.S. application Ser. No. 08/051,490, filed Apr. 22, 1993 now U.S. Pat. No. 5,308,826.

FIELD OF THE INVENTION

In one aspect, this invention relates to novel 4-substituted pyridyl-3-carbinols which exhibit unexpectedly desirable herbicidal activity. In other aspects, this invention relates to herbicidal compositions comprising a pyridyl carbinol and a suitable carrier, to herbicidal compositions comprising a pyridyl carbinol and a complementary herbicide, to a method of controlling undesirable vegetation comprising applying to the area where control is desired an herbicidally effective amount of a pyridyl carbinol compound and to intermediates useful in making such 4-substituted pyridyl-3-carbinol compounds.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide a novel herbicidal composition and a novel method of controlling weeds. Further, it is an object of this invention to provide intermediates which, as well as exhibiting herbicidal activity, are also useful in the production of other herbicidally active compounds.

While certain 4-substituted pyridyl-3-carbinols are disclosed in the art, these disclosures contain no description of the utility of such compounds. Thus, Radinov et al., "Synthesis of 4-Amino-3-pyridinyl and 4-Amino-5-pyrimidinyl Aryl Ketones and Related Compounds via an ortho-Lithiation Reaction", Synthesis, pp. 886–891, November 1986, disclose inter alia at page 887, compounds of the formula

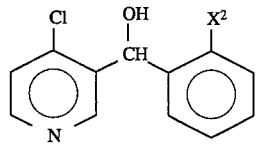

wherein $X^2$ is chlorine or fluorine.

Somewhat similarly, Marsais et al., "Directed Lithiation of 4-Halopyridines: Chemoselectivity, Regioselectivily and Application to Synthesis", J. Heterocyclic Chem., Vol 25, pp. 81–87 (1987), disclose the production of compounds of the formula

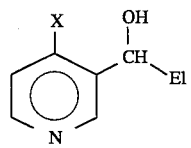

wherein El is phenyl or 2-methoxyphenyl.

Certain (non-substituted)-pyridyl-3-carbinols of the formula

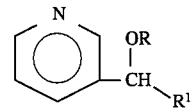

are disclosed in U.S. Pat. No. 4,407,806 to Cherpeck (wherein R and $R^1$ are as defined therein).

Similarly, U.S. Pat. No. 4,116,665 to Krumkalns discloses a method of regulating the growth of aquatic weeds employing compounds of the formula

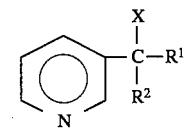

wherein, inter alia, $R^1$ may be hydrogen, $R^2$ may be (substituted)-phenyl and X may be hydroxyl or alkoxy.

SUMMARY OF THE INVENTION

In one aspect, this invention is directed to a compound of the formula (I):

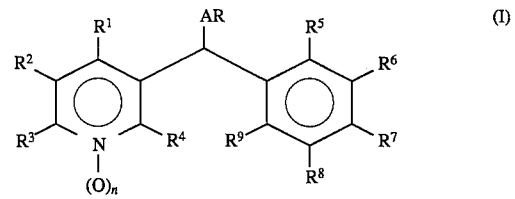

wherein:

$R^1$ and $R^5$ are each independently halogen, $C_1$–$C_6$ haloalkyl, $C_1$–$C_6$ alkyl, $C_1$–$C_6$ alkoxy, $C_1$–$C_6$ haloalkoxy, $(C_1$–$C_6)$alkoxy-$(C_1$–$C_6)$alkyl, —S(O)$_m$—$R^{10}$, cyano, —OH, thiocyano, nitro or —N($R^{11}$)($R^{12}$);

$R^2$, $R^3$ and $R^4$ are each independently hydrogen $C_1$–$C_6$ alkyl, nitro, halogen, $C_1$–$C_6$ alkoxy, $C_1$–$C_6$ haloalkoxy, $C_1$–$C_6$ haloalkyl or —S(O)$_m$—$R^{10}$;

$R^6$, $R^7$, and $R^8$ are each independently hydrogen halogen, $C_1$–$C_6$ alkyl, $C_1$–$C_6$ alkenyl, $C_1$–$C_6$ alkynyl, nitro, —N($R^{11}$)($R^{12}$), $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, halo$(C_1$–$C_6)$alkoxy-$(C_1$–$C_6)$alkyl, cyano, —C(X)—$R^{10}$ or —S(O)$_m$—$R^{10}$;

$R^9$ is hydrogen, halogen, $C_1$–$C_6$ alkyl, $C_1$–$C_6$ haloalkyl, $C_1$–$C_6$ alkoxy, $C_1$–$C_6$ haloalkoxy, $(C_1$–$C_6)$alkoxy-$(C_1$–$C_6)$-alkyl, —S(O)$_m$—$R^{10}$, cyano, hydroxy, thiocyano, nitro or —N($R^{11}$)($R^{12}$);

A is oxygen or sulfur;

n is 0 or 1;

R is hydrogen, hydrocarbyl, hydrocarbyl substituted with one or more of halogen or $C_1$–$C_6$ alkoxy or is of the formula —C(X)—$R^{10}$, —C(O)—C(O)—$R^{10}$, —S(O)$_2$—$R^{10}$ or —P(X)($R^{15}$)—($R^{16}$);

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula —N($R^{11}$)($R^{12}$);

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, $(C_1-C_6)$alkoxycarbonyl$(C_1-C_6)$alkyl, hydroxycarbonyl$(C_1-C_6)$alkyl, or $N(R^{13})(R^{14})$ wherein $R^{13}$ and $R^{14}$ are each independently hydrogen, $C_1-C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1-C_6$ alkyl;

$R^{15}$ and $R^{16}$ are each independently $C_1-C_6$ alkyl, $C_1-C_6$ alkylthio or $C_1-C_6$ alkoxy; and m is 0, 1 or 2;

with the proviso that when $R^1$ is chloro or fluoro; $R^5$ is hydrogen, chloro, fluoro or methoxy; and $R^2$, $R^3$, $R^6$, $R^7$, $R^8$ and $R^9$ are hydrogen; R is not hydrogen;

and agriculturally acceptable salts thereof.

In another aspect, this invention is directed to a herbicidal composition comprising:

(A) A compound of the formula (Ia):

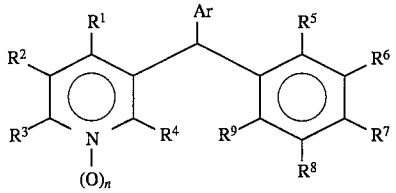

wherein:

$R^1$ and $R^5$ are each independently halogen, $C_1-C_6$ haloalkyl, $C_1-C_6$ alkyl, $C_1-C_6$ alkoxy, $C_1-C_6$ haloalkoxy, $(C_1-C_6)$-alkoxy-$(C_1-C_6)$alkyl, $-S(O)_m-R^{10}$, cyano, $-OH$, thiocyano, nitro or $-N(R^{11})(R^{12})$;

$R^2$, $R^3$ and $R^4$ are each independently hydrogen, $C_1-C_6$ alkyl, nitro, halogen, $C_1-C_6$ alkoxy, $C_1-C_6$ haloalkoxy, $C_1-C_6$ haloalkyl or $-S(O)_m-R^{10}$;

$R^6$, $R^7$, and $R^8$ are each independently hydrogen, halogen, $C_1-C_6$ alkyl, $C_1-C_6$ alkenyl, $C_1-C_6$ alkynyl, nitro, $-N(R^{11})(R^{12})$, $C_1-C_6$ haloalkyl, $C_1-C_6$ alkoxy, $C_1-C_6$ haloalkoxy, $(C_1-C_6)$alkoxy-$(C_1-C_6)$alkyl, halo$(C_1-C_6)$alkoxy-$(C_1-C_6)$alkyl, cyano, $-C(X)-R^{10}$ or $-S(O)_m-R^{10}$;

$R^9$ is hydrogen, halogen, $C_1-C_6$ alkyl, $C_1-C_6$ haloalkyl, $C_1-C_6$ alkoxy, $C_1-C_6$ haloalkoxy, $(C_1-C_6)$alkoxy-$(C_1-C_6)$alkyl, $-S(O)_m-R^{10}$, cyano, hydroxy, thiocyano, nitro or $-N(R^{11})(R^{12})$;

A is oxygen or sulfur;

n is 0 or 1;

R is hydrogen, hydrocarbyl, hydrocarbyl substituted with one or more of halogen or $C_1-C_6$ alkoxy or is of the formula $-C(X)-R^{10}$, $-C(O)-C(O)-R^{10}$, $-S(O)_2-R^{10}$ or $-P(X)(R^{15})-(R^{16})$;

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula $-N(R^{11})(R^{12})$;

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, $(C_1-C_6)$-alkoxycarbonyl$(C_1-C_6)$alkyl, hydroxycarbonyl$(C_1-C_6)$alkyl, or $N(R^{13})(R^{14})$ wherein $R^{13}$ and $R^{14}$ are each independently hydrogen, $C_1-C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1-C_6$ alkyl;

$R^{15}$ and $R^{16}$ are each independently $C_1-C_6$ alkyl, $C_1-C_6$ alkylthio or $C_1-C_6$ alkoxy; and m is 0, 1 or 2;

or an agriculturally acceptable salt thereof; and (B) a carrier therefor.

This invention also is directed to herbicidal compositions comprising a compound of formula (I), as defined above, together with a complementary herbicide, and an agriculturally acceptable carrier therefor.

In yet another aspect, this invention is directed to a method for controlling undesirable vegetation comprising applying to the area where control is desired an herbicidally effective amount of a compound of the formula (Ia):

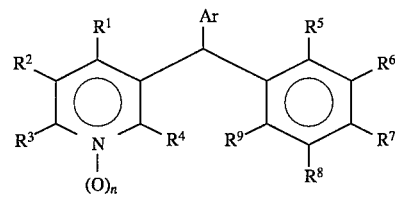

wherein $R^1$ and $R^5$ are each independently halogen, $C_1-C_6$ haloalkyl, $C_1-C_6$ alkyl, $C_1-C_6$ alkoxy, $C_1-C_6$ haloalkoxy, $(C_1-C_6)$alkoxy-$(C_1-C_6)$alkyl, $-S(O)_m-R_{10}$, cyano, $-OH$, thiocyano, nitro or $-N(R^{11})(R^{12})$;

$R^2$, $R^3$ and $R^4$ are each independently hydrogen $C_1-C_6$ alkyl, nitro, halogen, $C_1-C_6$ alkoxy, $C_1-C_6$ haloalkoxy, $C_1-C_6$ haloalkyl or $-S(O)_m-R^{10}$;

$R^6$, $R^7$, and $R^8$ are each independently hydrogen, halogen, $C_1-C_6$ alkyl, $C_1-C_6$ alkenyl, $C_1-C_6$ alkynyl, nitro, $-N(R^{11})(R^{12})$, $C_1-C_6$ haloalkyl, $C_1-C_6$ alkoxy, $C_1-C_6$ haloalkoxy, $(C_1-C_6)$alkoxy-$(C_1-C_6)$alkyl, halo$(C_1-C_6)$alkoxy-$(C_1-C_6)$alkyl, cyano, $-C(X)-R^{10}$ or $-S(O)_m-R^{10}$;

$R^9$ is hydrogen, halogen, $C_1-C_6$ alkyl, $C_1-C_6$ haloalkyl, $C_1-C_6$ alkoxy, $C_1-C_6$ haloalkoxy, $(C_1-C_6)$alkoxy-$(C_1-C_6)$alkyl, $-S(O)_m-R^{10}$, cyano, hydroxy, thiocyano, nitro or $-N(R^{11})(R^{12})$;

A is oxygen or sulfur;

n is 0 or 1;

R is hydrogen, hydrocarbyl, hydrocarbyl substituted with one or more of halogen or $C_1-C_6$ alkoxy or is of the formula $-C(X)-R^{10}$, $-C(O)-C(O)-R^{10}$, $-S(O)_2-R^{10}$ or $-P(X)(R^{15})(R^{16})$;

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula $-N(R^{11})(R^{12})$;

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, $(C_1-C_6)$-alkoxycarbonyl$(C_1-C_6)$alkyl, hydroxycarbonyl$(C_1-C_6)$alkyl, or $N(R^{13})(R^{14})$ wherein $R^{13}$ and $R^{14}$ are each independently hydrogen, $C_1$–$C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1$–$C_6$ alkyl;

$R^{15}$ and $R^{16}$ are each independently $C_1$–$C_6$ alkyl, $C_1$–$C_6$ alkylthio, or $C_1$–$C_6$ alkoxy; and m is 0, 1 or 2;

and agriculturally acceptable salts thereof.

In yet a further aspect, because the compounds of this invention wherein AR is OH are useful intermediates for producing the other compounds of this invention, as well as possessing herbicidal activity, this invention is directed to a compound of the formula (II):

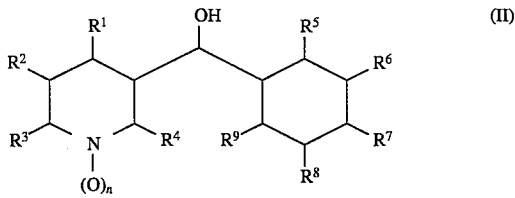

wherein $R^1$ and $R^5$ are each independently halogen, $C_1$–$C_6$ haloalkyl, $C_1$–$C_6$ alkyl, $C_1$–$C_6$ alkoxy, $C_1$–$C_6$ haloalkoxy, $(C_1$–$C_6)$alkoxy-$(C_1$–$C_6)$alkyl, —S(O)$_m$—R$^{10}$, cyano, —OH, thiocyano, nitro or —N(R$^{11}$)(R$^{12}$);

$R^2$, $R^3$ and $R^4$ are each independently hydrogen $C_1$–$C_6$ alkyl, nitro, halogen, $C_1$–$C_6$ alkoxy, $C_1$–$C_6$ haloalkoxy, $C_1$–$C_6$ haloalkyl or —S(O)$_m$—R$^{10}$;

$R^6$, $R^7$, and $R^8$ are each independently hydrogen, halogen, $C_1$–$C_6$ alkyl, $C_1$–$C_6$ alkenyl, $C_1$–$C_6$ alkynyl, nitro, —N(R$^{11}$)(R$^{12}$), $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, halo$(C_1$–$C_6)$alkoxy-$(C_1$–$C_6)$alkyl, cyano, —C(X)—R$^{10}$ or —S(O)$_m$—R$^{10}$;

$R^9$ is hydrogen, halogen, $C_1$–$C_6$ alkyl, $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, —S(O)$_m$—R$^{10}$, cyano, hydroxy, thiocyano, nitro or —N(R$^{11}$)(R$^{12}$);

n is 0 or 1;

$R^{10}$ is hydrocarbyl, substituted hydrocarbyl, hydrocarbyloxy, substituted hydrocarbyloxy, hydrocarbyl-S—, substituted hydrocarbyl-S— or is of the formula —N(R$^{11}$)(R$^{12}$);

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, $(C_1$–$C_6)$alkoxycarbonyl$(C_1$–$C_6)$ alkyl, hydroxycarbonyl$(C_1$–$C_6)$alkyl, or N(R$^{13}$)(R$^{14}$) wherein $R^{13}$ and $R^{14}$ are each independently hydrogen, $C_1$–$C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, and of which may be optionally substituted with $C_1$–$C_6$ alkyl;

$R^{15}$ and $R^{16}$ are each independently $C_1$–$C_6$ alkyl, $C_1$–$C_6$ alkylthio, or $C_1$–$C_6$ alkoxy; and m is 0, 1 or 2;

with the proviso that when $R^5$ is hydrogen, chloro, fluoro or methoxy; and $R^2$, $R^3$, $R^6$, $R^7$, $R^8$ and $R^9$ are hydrogen; $R^1$ is not chloro or fluoro;

and agriculturally acceptable salts thereof.

DETAILED DESCRIPTION OF THE PREFERRED EMBODIMENTS

The novel herbicidal compounds of this invention are the formula (I):

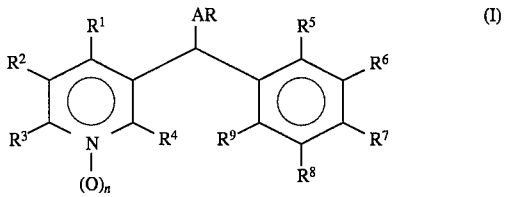

wherein:

$R^1$ and $R^5$ are each independently halogen, $C_1$–$C_6$ haloalkyl, $C_1$–$C_6$ alkyl, $C_1$–$C_6$ alkoxy, $C_1$–$C_6$ haloalkoxy, $(C_1$–$C_6)$-alkoxy-$(C_1$–$C_6)$alkyl, —S(O)$_m$—R$^{10}$, cyano, —OH, thiocyano, nitro or —N(R$^{11}$)(R$^{12}$);

$R^2$, $R^3$ and $R^4$ are each independently hydrogen, $C_1$–$C_6$ alkyl, nitro, halogen, $C_1$–$C_6$ alkoxy, $C_1$–$C_6$ haloalkoxy, $C_1$–$C_6$ haloalkyl or —S(O)$_m$—R$^{10}$;

$R^6$, $R^7$, and $R^8$ are each independently hydrogen, halogen, $C_1$–$C_6$ alkyl, $C_1$–$C_6$ alkenyl, $C_1$–$C_6$ alkynyl, nitro, —N(R$^{11}$)(R$^{12}$), $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, halo$(C_1$–$C_6)$alkoxy-$(C_1$–$C_6)$alkyl, cyano, —C(X)—R$^{10}$ or —S(O)$_m$—R$^{10}$;

$R^9$ is hydrogen, halogen, $C_1$–$C_6$ alkyl, $C_1$–$C_6$ haloalkyl, $C_1$–$C_6$ alkoxy, $C_1$–$C_6$ haloalkoxy, $(C_1$–$C_6)$alkoxy-$(C_1$–$C_6)$alkyl, —S(O)$_m$—R$^{10}$ cyano hydroxy, thiocyano, nitro or —N(R$^{11}$)(R$^{12}$);

A is oxygen or sulfur;

n is 0 or 1;

R is hydrogen, hydrocarbyl, hydrocarbyl substituted with one or more of halogen or $C_1$–$C_6$ alkoxy or is of the formula —C(X)—R$^{10}$, —C(O)—C(O)—R$^{10}$, —S(O)$_2$—R$^{10}$ or —P(X)(R$^{15}$)(R$^{16}$);

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula —N(R$^{11}$)(R$^{12}$);

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, $(C_1$–$C_6)$alkoxycarbonyl$(C_1$–$C_6)$alkyl, hydroxycarbonyl$(C_1$–$C_6)$alkyl, or N(R$^{13}$)(R$^{14}$) wherein $R^{13}$ and $R^{14}$ are each independently hydrogen, $C_1$–$C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1$–$C_6$ alkyl;

$R^{15}$ and $R^{16}$ are each independently $C_1$–$C_6$ alkyl, $C_1$–$C_6$ alkylthio; or $C_1$–$C_6$ alkoxy; and m is 0, 1 or 2;

with the proviso that when $R^1$ is chloro or fluoro; $R^5$ is hydrogen, chloro, fluoro or methoxy; and $R^2$, $R^3$, $R^6$, $R^7$, $R^8$ and $R^9$ are hydrogen; R is not hydrogen;

and agriculturally acceptable salts thereof.

Preferably, $R^1$ is halogen;

$R^2$, $R^3$ and $R^4$ are hydrogen;

$R^5$ is halogen, $C_1$–$C_6$ alkyl, $C_1$–$C_6$ haloalkyl, $C_1$–$C_6$ alkoxy, $C_1$–$C_6$ haloalkoxy, nitro or —S(O)$_m$—($C_1$–$C_3$)alkyl wherein m is 0, 1 or 2;

$R^6$, $R^7$, $R^8$ and $R^9$ are each independently hydrogen, $C_1$–$C_6$ alkyl, halogen or $C_1$–$C_6$ alkoxy; and R is phenyl-($C_1$–$C_3$)alkyl or is of the formula

wherein $R^{12}$ is $C_1$–$C_{12}$ alkyl, $C_1$–$C_6$ haloalkyl, phenyl or is of the formula

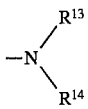

wherein $R^{13}$ and $R^{14}$ are each independently $C_1$–$C_{12}$ alkyl, hydrogen $C_2$–$C_{12}$ alkenyl, $C_2$–$C_{12}$ alkynyl, $C_1$–$C_{12}$ haloalkyl, $C_1$–$C_6$ alkoxy, ($C_1$–$C_6$)alkoxy($C_1$–$C_6$)alkyl or $R^{13}$ and $R^{14}$ together with the nitrogen to which they are bound form a morpholine, piperidine or pyrrolidine ring.

More preferably, $R^1$ is chloro or bromo;

$R^5$ is trifluoromethyl, trifluoromethoxy, chloro, bromo, methoxy, methyl or ethyl;

$R^2$, $R^3$, $R^4$, $R^7$ and $R^8$ are hydrogen;

$R^6$ and $R^9$ are each independently hydrogen, chloro or methyl; and

R is benzyl or is of the formula

wherein $R^{12}$ is $C_1$–$C_6$ alkyl or is of the formula

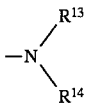

wherein $R^{13}$ and $R^{14}$ are independently hydrogen, phenyl, $C_1$–$C_6$ haloalkyl or $C_1$–$C_6$ alkyl or together $R^{13}$ and $R^{14}$ form a morpholine ring.

Particularly preferred compounds include;

4-chloro-3-(1-N,N-dimethylcarbamyloxy-2'-trifluoromethylbenzyl)-pyridine;

4-chloro-3-(1-N-methylcarbamyloxy-2'-trifluoromethylbenzyl)-pyridine;

4-chloro-3-(1-N,N-diethylcarbamyloxy-2'-trifluoromethylbenzyl)-pyridine;

4-chloro-3-[1-(4-morpholine)-carbonyloxy-2'trifluoromethylbenzyl]-pyridine;

4-chloro-3-(1-N-methyl-N-phenyl-carbamyloxy-2'-trifluoromethylbenzyl)-pyridine;

4-chloro-3-(1-trimethylacetoxy-2'-trifluoromethylbenzyl)-pyridine;

4-chloro-3-[1-(2-N-chloroethylcarbamyloxy)-2'trifluoromethylbenzyl]-pyridine;

4-chloro-3-(1-N-ethylcarbamyloxy-2'trifluoromethylbenzyl)-pyridine;

4-chloro-3-(1-N-isopropylcarbamyloxy-2'-trifluoromethylbenzyl)-pyridine;

4-chloro-3-(1-N-propylcarbamyloxy-2'-trifluoromethylbenzyl)-pyridine;

4-bromo-3-(1-N,N-dimethylcarbamyloxy-2'-trifluoromethylbenzyl)-pyridine;

4-chloro-3-(1-N,N-dimethyl-carbamyloxy-2'-chlorobenzyl)pyridine;

4-chloro-3-(1-N,N-dimethylcarbamyloxy-2'-methylbenzyl)-pyridine;

4-chloro-3-(1-N-methylcarbamyloxy-2'-bromobenzyl)pyridine;

4-chloro-3-(1-N,N-diallylcarbamyl-2'-trifluoromethylbenzyl)-pyridine;

4-chloro-3-(1-N-methyl-N-ethyl-carbamyloxy-2'-trifluoromethylbenzyl)-pyridine;

4-chloro-3-(1-N-allylcarbamyloxy-2'-trifluoromethylbenzyl)-pyridine; and 4-chloro-3-(1-t-butylcarbonyloxy-2'-ethylbenzyl)pyridine.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

The compounds of such formulae can exist in enantiomeric forms. The invention includes both individual enantiomers and mixtures of the two in all proportions.

As is employed herein, the term "hydrocarbyl", whether representing a substituent on its own or whether it is part of the definition of a larger group (e.g., as in hydrocarbyloxy, hydrocarbyl-S(O)$_m$—, etc.) is intended to include hydrocarbyl groups having from 1 to 12 carbon atoms. The term hydrocarbyl therefore includes, for example, $C_1$ to $C_{12}$ alkyl including both straight and branched chain isomers (e.g., methyl, ethyl, propyl, and hexyl); cycloalkyl of 3 to 12 carbon atoms (e.g., cyclopropyl, cyclobutyl and cyclohexyl); $C_2$ to $C_{12}$ alkenyl including for example allyl and crotyl; $C_2$ to $C_{12}$ alkynyl (e.g., propynyl); phenyl; phenylalkyl; alkylphenyl, alkenylphenyl, alkynylphenyl, alkylbenzyl, alkenylbenzyl, alkynyl benzyl, naphthyl and the like.

The term "substituted hydrocarbyl" is intended to include hydrocarbyl groups, as defined above, having one or more substituents selected from the group consisting of halogen (i.e., fluorine, chlorine, bromine, and iodine); $C_{1-4}$ alkoxy; $C_{1-4}$ alkyl-S(O)$_m$—; cyano; carboxy, and salts, amides and esters thereof; alkanoyl of 2 to 4 carbon atoms; and phenyl optionally substituted by one or more $C_{1-4}$ alkyl, $C_{1-4}$ alkoxy, $C_{1-4}$ alkyl-S(O)$_m$—, nitro, fluorine, chlorine, bromine, cyano, or $CF_3$ groups. In the above definitions, m is 0, 1 or 2.

Further, when the hydrocarbyl radical is a substituted aryl radical (e.g., phenyl, benzyl or naphthyl), the substituents may include one or more of the substituents listed in the last foregoing paragraph, and may also include nitro.

The expression "salts, amides, and esters thereof" used above in relation to carboxy substitution includes, for example, salts formed from alkali metal (e.g., sodium, potassium, and lithium), alkaline earth metals (e.g., calcium and magnesium), the ammonium ion, and substituted ammonium ions wherein one, two, three, or four of the hydrogen atoms have been replaced by optionally substituted $C_{1-6}$ hydrocarbyl moieties as defined above.

Further, the above definitions the term "halogen" includes fluoro, chloro, bromo and iodo groups. In polyhalogenated groups the halogens may be the same or different.

The compounds of the present invention have been found to be active herbicides, possessing utility as pre-emergence and post-emergence herbicides and useful against a wide range of plant species including broadleaf and grassy species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalogen, acetic, sulfonic, phosphonic, inorganic and organic acid salts.

In general, the compounds of this invention are prepared by (A) reacting a substituted pyridine of the formula (III):

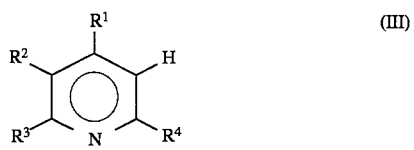

with a substituted benzaldehyde of the formula (IV):

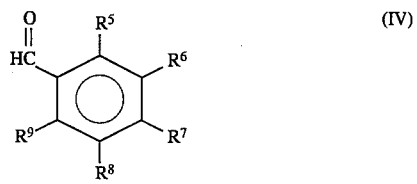

wherein $R^1$, $R^2$, $R^3$, $R^4$, $R^5$, $R^6$, $R^7$, $R^8$ and $R^9$ are as defined for formula (I) above; in the presence of a suitable base to form a 3-pyridyl carbinol of formula II above (without the proviso thereto being applicable); and, where appropriate, (B) reacting such pyridyl carbinol with an appropriate derivatizing agent (e.g., an alkyl or aryl acid halide, carbamoyl halide, alkyl halide, sulfonyl halide or phosphoryl halide) or an appropriate isocyanate, or sequentially first with phosgene or a phosgene equivalent and then with an appropriate amine, to produce the desired compound.

Typically, about 1–2 equivalents of an appropriate base (such as lithium diisopropylamide or n-butyl lithium) is added to a substituted pyridine of formula (III) in a solvent (such as ethylene glycol dimethyl ether, tetrahydrofuran, diethyl ether or the like) at a temperature of between about –100° and about –40° C. After suitable blending, about 1–2 equivalents of the substituted benzaldehyde (IV) is generally added.

This reaction mixture is typically agitated and slowly warmed up to ambient temperature (about 25° C.) over a period of 1–24 hours. The reaction is then generally quenched by the addition of a saturated aqueous ammonium chloride solution or aqueous hydrochloric acid. The pyridyl carbinol so produced may be recovered by conventional techniques (such as extraction, filtration and the like) and purified by known methods, e.g., flash chromatography.

In the second step, the pyridyl carbinol (II), in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as a carbamoyl halide, an alkyl halide, sulfonyl halide or a phosphophoryl halide, an alkyl or aryl acid halide) is then added and the mixture agitated until complete. The reaction may be quenched by the addition of ice water, and the products recovered by conventional techniques, such as extraction, filtration and the like. The product so recovered may then be purified by conventional techniques such as flash chromatography or the like.

Alternatively, in the second step, the pyridyl carbinol in suitable solvent (such as tetrahydrofuran, methylene chloride or the like) may be added to between about 2 and about 3 equivalents of an appropriate isocyanate. Between about 1 and about 10 mole percent of one or more appropriate catalyst, e.g., triethyl amine or dibutyl tin dilaurate, may be added and the reaction mixture agitated at between about 0° and 100° C. for an appropriate period (e.g., 2 to 24 hours). The product may be recovered by conventional techniques (such as extraction, filtration or the like) and may be purified by conventional techniques such as flash chromatography or the like.

The substituted pyridine starting materials of Formula (III) are either commercially available or may be prepared by one of ordinary skill in the art employing methods such as those described in "Heterocyclic Compounds, Pyridine and its Derivatives", R. A. Abramovitch, Vol 14, Wiley, 1973. The aldehyde starting materials of Formula (IV) are commercially available or may be prepared employing techniques such as those described in "Survey of Organic Synthesis", C. A. Buehler et al., Vols. 1 and 2, Wiley-Interscience, 1970.

The compositions of this invention comprise a compound of formula (Ia) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplet are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrenebutadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, desiccants and plant growth inhibitors with which the compounds of this invention can be combined are:

Examples of useful complementary herbicides include:

A. Benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

* These compounds are preferably employed in combination with a safener such as 2,2-dichloro-N,N-di-2-propenylacetamide (dichlormid).

Of the above complementary herbicides, the following are preferred co-herbicides for use in an herbicidal composition containing a compound of formula (I): anilide herbicides, triketone and cyclohexanedione herbicides, imidazolidinone herbicides, sulfonylurea herbicides and phenoxyphenoxypropionate herbicides. From these classes of preferred co-herbicides, specific examples of preferred co-herbicides for use in combination with the pyridyl carbinols of this invention are metolachlor, imazaquin, bensulfuron and the methyl ester thereof, chlorsulfuron and dichlofop.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

Wettable powders:

| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethyleneethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

Emulsifiable concentrate:

| 25%: | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

The amount of the present compositions which constitute a herbicidally effective amount depends upon the nature of the seeds or plants to be controlled. The rate of application of active ingredients varies from about 0.01 to about pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

EXAMPLE 1

Preparation of
4-chloro-3-(1-hydroxy-2',6'-dichlorobenzyl)-pyridine (Compound No. 11)

Eighteen grams of 4-chloro pyridine hydrochloride were placed into 100 ml of diethyl ether in a 500 ml beaker equipped with a magnetic stirrer. 6.5 grams of sodium hydroxide in 100 ml (milliliters) of water were added at 0° C. and the mixture stirred for 15 minutes. The diethyl ether layer was separated and washed with water, dried over magnesium sulfate and filtered and stripped. 5.7 grams of the 4-chloropyridine produced was placed into a 3-neck flask in 50 ml of ethylene glycol dimethyl ether and cooled to −70° C. Forty ml of lithium diisopropyl amide ("LDA") was added over a period of 30 minutes while the temperature maintained at −60° C. to produce an orange suspension. The reaction mixture was then stirred at −70° C. for one hour. 9.2 grams of 2,6-dichlorobenzaldehyde were added and the temperature maintained between −45° to −60° C. The reaction mixture was stirred in a dry ice bath for 2 hours, then left at room temperature overnight.

Thirty-five ml of saturated aqueous ammonium chloride solution was added to the reaction mixture, and the mixture stirred for 15 minutes at room temperature. The solid was removed by filtration and washed twice, first with water, then with methylene chloride to yield 13.2 grams of 4-chloro-3-(1-hydroxy-2',6'-dichloro-2 benzyl)pyridine.

EXAMPLE 2

Preparation of
4-chloro-3-(1-N,N-dimethylcarbamyloxy-2',6'-dichloro-benzyl)-pyridine (Compound No. 77)

One gram of 4-chloro-3-(1-hydroxy-2',6'-dichlorobenzyl)-pyridine was dissolved in 20 ml of tetrahydrofuran in a 200 ml round bottom flask equipped with a magnetic stirrer. The solution was cooled in an ice bath, and 0.3 gram of sodium hydride added. The temperature was maintained at 0° C. and 0.55 ml of N,N-dimethyl carbamyl chloride added. The mixture was stirred at room temperature overnight, poured into ice and extracted with methylene chloride twice. The combined methylene chloride layers were separated and washed with water, dried with magnesium sulfate, filtered and stripped to yield a yellow oil, 4-chloro-3-(1-N,N-dimethylcarbamyloxy-2',6'-dichloro-benzyl)-pyridine.

EXAMPLE 3

Preparation of
2-chloro-3-(1-hydroxy-2'-trifluoromethyl-benzyl)-4-trifluoromethyl-pyridine (Compound No. 13)

To a 3-neck flask equipped with a dropping funnel, a thermometer, and a condenser with a drying tube were added 5 grams of 2-chloro-4-trifluoromethyl pyridine and 5 ml of ethylene glycol dimethyl ether. The mixture was cooled to −70° C. and 22 ml of LDA were slowly added with the temperature maintained below −55° C. The reaction mixture was stirred at −70° C. for 1.5 hours, and 3.5 ml of 2-trifluoromethyl benzaldehyde added. The reaction mixture was stirred in a dry-ice bath, then at room temperature over night. Fifteen ml of saturated aqueous ammonium chloride solution was added, the solvent stripped and the oil residue washed with water and extracted with methylene chloride (3 times). The combined methylene chloride layers were washed with brine, dried and stripped to yield a brown oil. The brown oil was put onto a silica gel column and eluted with a 1:1 mixture of hexane and diethyl ether to yield 6.2 grams of 2-chloro-3-(1-hydroxy-2'-trifluoromethyl-benzyl)-4-trifluoro methyl-pyridine.

EXAMPLE 4

Preparation of
2-chloro-3-[1-(4-morpholine)-carbonyloxy-2'-trifluoromethyl-benzyl]-4-trifluoromethyl pyridine (Compound No. 87)

To a 200 ml round bottom flask with magnetic stirrer reactor was added 1.0 gram of 2-chloro-3-(1-hydroxy-2'-trifluoromethyl-benzyl)-4-trifluoromethyl pyridine dissolved in 20 ml tetrahydrofuran. The solution was cooled in ice, and 0.3 gram of sodium hydride added. 0.5 ml of morpholine carbamyl chloride was added at 0° C., and the mixture stirred at room temperature overnight. An orange participate formed and the mixture was poured into ice water, and extracted two times with methylene chloride. The combined methylene chloride layers were washed with water, dried (over magnesium sulfate), filtered and stripped to yield 1.5 grams of an orange solid, 2-chloro-3-[1-(4-morpholine)-carbonyloxy-2'-trifluoromethylbenzyl]-4-trifluoromethyl pyridine.

EXAMPLE 5

Preparation of
4-chloro-3-(1-N,N-diallylcarbamyloxy-2'-trifluoromethyl-benzyl)-pyridine (Compound No. 48)

To 4 grams of phosgene (20% in toluene) cooled in an ice bath were added, over a 5 minute period, 2 grams of 2-chloro-3-(1-hydroxy-2'-trifluoromethyl-benzyl)-pyridine (produced in accordance with the process of Example 1 employing 2-trifluoromethyl benzaldehyde as a starting material) dissolved in 25 ml of tetrahydrofuran. One gram of triethylamine was added and the mixture stirred over night at room temperature. Seven ml of diallylamine were added to form a yellow suspension. This suspension was stripped and the mixture triturated in diethyl ether. The solid was filtered and rinsed with diethyl ether. The filtrate was stripped, put on a silica gel column, and eluted with a 10:1 hexane:ethyl acetate mixture to yield 2.25 grams of 4-chloro-3-(1-N,N-diallylcarbamyloxy-2'-trifluoromethyl-benzyl)-pyridine.

EXAMPLE 6

Preparation of
4-chloro-3-[1-(2-N-chloroethylcarbamyloxy)-2'-trifluoromethyl-benzyl]-pyridine (Compound No. 41)

To 1.2 grams of 4-chloro-3-(1-hydroxy-2'-trifluoromethyl-benzyl)-pyridine dissolved in 10 ml of tetrahydrofuran were added 2 equivalents of 2-chloroethyl isocyanate along with 3 drops of triethylamine and 2 drops of dibutyl tin dilaurate. The mixture was stirred at room temperature overnight and, in 20 ml of methylene chloride were added with an additional 2 equivalents of 2-chloroethyl isocyanate, 3 drops of triethylamine and 2 drops of dibutyl tin dilaurate. The mixture was again stirred overnight; then poured into ice water; extracted twice with methylene chloride, dried and stripped. The residue was put onto a silica gel column and eluted with a 4:1 hexane:diethyl ether mixture to yield 0.9 grams of 4-chloro-3-[1-(2-N-chloroethylcarbamyloxy)-2'-trifluoromethylbenzyl]-pyridine.

EXAMPLE 7

Preparation of
4-chloro-3-(1-N,N-dimethylcarbamyloxy-2'-trifluoromethyl-benzyl)-pyridine (Compound No. 27)

1.5 grams of 4-chloro-3-(1-hydroxy-2'-trifluoromethyl-benzyl)-pyridine were dissolved in 25 ml of tetrahydrofuran and cooled to 0° C. 0.5 gram of sodium hydride was added and the mixture stirred for 15 minutes. 0.75 ml of N,N-dimethyl carbamyl chloride was added and the mixture was stirred overnight at room temperature. The mixture was then poured into ice water and extracted with methylene chloride. The methylene chloride layer was washed with water, dried over magnesium sulfate, filtered and stripped to yield an orange colored solid. The solid was rinsed with hexane to yield 1.53 grams of 4-chloro-3-(1-N,N-dimethylcarbamyloxy-2'-trifluoromethyl-benzyl)-pyridine.

EXAMPLE 8

Preparation of 4-chloro-3-(1-trimethylacetoxy-2'-trifluoromethyl-benzyl)-pyridine (Compound No. 39)

2.0 grams of 4-chloro-3-(1-hydroxy-2'-trifluoromethyl-benzyl)-pyridine was dissolved in 40 ml of tetrahydrofuran and cooled to 0° C. 0.7 g of sodium hydride was added and the mixture stirred for 15 minutes. 1.30 ml of trimethyl acetyl chloride was added and the reaction was stirred overnight at room temperature. The reaction mixture was poured into ice water and extracted two times with methylene chloride. The combined methylene chloride layers were washed with water; dried over magnesium sulfate; filtered and stripped to yield a yellow oil, 4-chloro-3-(1-trimethylacetoxy-2'-trifluoromethyl-benzyl-pyridine.

EXAMPLE 9

Preparation of 4-chloro-3-(1-benzyloxy-2'-trifluoromethyl-benzyl)-pyridine (Compound No. 57)

0.9 grams of sodium hydride (80% in white oil) was rinsed 4 times with 2 ml of tetrahydrofuran. Over a 2 minute period, 2.9 grams of 2-chloro-3-(1-hydroxy-2'-trifluoromethylbenzyl)-pyridine were added and the mixture refluxed for 5 minutes and stirred for 1 hour at ambient temperature. Benzyl bromide (1.7 ml) was added and the mixture stirred for 1 hour and then refluxed for 0.5 hour. 0.1 gram of sodium iodide was added and the mixture stirred for 0.5 hour. The mixture was then stripped and dissolved in a water/methylene chloride mixture. The organic layer was washed with brine and dried over magnesium sulfate. The product was filtered, stripped, placed on a silica gel column and eluted with a 1:2 hexane:ethylacetate blend to yield 3.2 grams of 4-chloro-3-(1-benzyloxy-2'-trifluoromethyl-benzyl)-pyridine.

EXAMPLE 10

Employing a process similar to those described above, the following compounds, listed in Table I, were prepared:

TABLE I

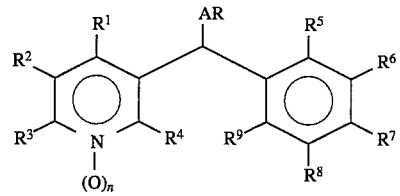

(I)

| COMP. NO. | n | $R^1$ | $R^2$ | $R^3$ | $R^4$ | $R^5$ | $R^6$ | $R^7$ | $R^8$ | $R^9$ | R |
|---|---|---|---|---|---|---|---|---|---|---|---|
| Compounds where A is —O— | | | | | | | | | | | |
| 1 | 0 | Cl | H | H | H | —CH$_3$ | H | Cl | H | H | H |
| 2 | 0 | Cl | H | H | H | —CH$_3$ | H | H | H | H | H |
| 3 | 0 | Cl | H | H | H | —OCH$_3$ | H | —OCH$_3$ | H | H | H |
| 4 | 0 | Cl | H | H | H | —CF$_3$ | H | H | H | H | H |
| 5 | 0 | Cl | H | H | H | —NO$_2$ | H | —CF$_3$ | H | H | H |
| 6 | 0 | Cl | H | H | H | Cl | —OCH$_2$CH$_3$ | Br | H | H | H |
| 7 | 0 | Br | H | H | H | —CF$_3$ | H | H | H | H | H |
| 8 | 0 | —C$_4$H$_9$ | H | H | H | —CF$_3$ | H | H | H | H | H |

TABLE I-continued

Structure (I):

Pyridine ring with R¹ (position 4), R² (position 5), R³ (position 6), R⁴ (position 2), N with (O)ₙ; linked via CH(AR) to phenyl ring bearing R⁵, R⁶, R⁷, R⁸, R⁹.

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 9  | 0 | Cl    | H | H | H | Cl     | H | H | H | H    | H |
| 10 | 0 | Cl    | H | H | H | Br     | H | H | H | H    | H |
| 11 | 0 | Cl    | H | H | H | Cl     | H | H | H | Cl   | H |
| 12 | 1 | Cl    | H | H | H | —CF₃   | H | H | H | H    | H |
| 13 | 0 | —CF₃  | H | H | Cl| CF₃    | H | H | H | H    | H |
| 14 | 0 | Cl    | H | H | H | —C₂H₅  | H | H | H | H    | H |
| 15 | 0 | Cl    | H | H | H | —CH₃   | H | H | H | —CH₃ | H |
| 16 | 0 | Cl    | H | H | H | —OCH₃  | H | H | H | H    | H |
| 17 | 0 | Cl    | H | H | H | —OCF₃  | H | H | H | H    | H |
| 18 | 0 | Cl    | H | H | H | F      | H | H | H | H    | H |
| 19 | 0 | —SCH₃ | H | H | H | —CF₃   | H | H | H | H    | H |
| 20 | 0 | Cl    | H | H | H | —SC₂H₅ | H | H | H | H    | H |
| 21 | 0 | Cl    | H | H | H | —CF₃   | H | H | H | H    | —C(=O)CH₃ |
| 22 | 0 | Cl    | H | H | H | —CF₃   | H | H | H | H    | —C(=O)—CHCl₂ |
| 23 | 0 | Cl    | H | H | H | —CF₃   | H | H | H | H    | —C(=O)—CH₂Cl |
| 24 | 0 | Cl    | H | H | H | —CF₃   | H | H | H | H    | —C(=O)-(2,4-dichlorophenyl) |
| 25 | 0 | Cl    | H | H | H | —CF₃   | H | H | H | H    | —C(=O)-(2-nitro-4-chlorophenyl) |
| 26 | 0 | Cl    | H | H | H | —CF₃   | H | H | H | H    | —S(=O)₂-(4-chlorophenyl) |
| 27 | 0 | Cl    | H | H | H | —CF₃   | H | H | H | H    | —C(=O)—N(CH₃)₂ |
| 28 | 0 | Cl    | H | H | H | —CF₃   | H | H | H | H    | —S(=O)(=O)CH₃ |
| 29 | 0 | Cl    | H | H | H | —CF₃   | H | H | H | H    | —C(=O)—C(=O)—OC₂H₅ |
| 30 | 0 | Cl    | H | H | H | —CF₃   | H | H | H | H    | —C(=O)—OC₂H₅ |
| 31 | 0 | Cl    | H | H | H | —CF₃   | H | H | H | H    | —C(=O)—N(H)(CH₃) |

TABLE I-continued

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 32 | 0 | Cl | H | H | H | —CF₃ | H | H | H | H | —C(=O)—N(C₂H₅)₂ |
| 33 | 0 | Cl | H | H | H | —CF₃ | H | H | H | H | —C(=S)—N(CH₃)₂ |
| 34 | 0 | Cl | H | H | H | —CF₃ | H | H | H | H | —C(=O)—NH—(4-Cl-C₆H₄) |
| 35 | 0 | Cl | H | H | H | —CF₃ | H | H | H | H | —C(=O)—CH(CH₃)₂ |
| 36 | 0 | Cl | H | H | H | —CF₃ | H | H | H | H | —C(=O)—S—CH(CH₃)₂ |
| 37 | 0 | Cl | H | H | H | —CF₃ | H | H | H | H | —C(=O)—N(morpholino) |
| 38 | 0 | Cl | H | H | H | —CF₃ | H | H | H | H | —C(=O)—N(CH₃)(C₆H₅) |
| 39 | 0 | Cl | H | H | H | —CF₃ | H | H | H | H | —C(=O)—C(CH₃)₃ |
| 40 | 0 | Cl | H | H | H | —CF₃ | H | H | H | H | —P(=O)(OC₂H₅)₂ |
| 41 | 0 | Cl | H | H | H | —CF₃ | H | H | H | H | —C(=O)—NH—CH₂—CH₂Cl |
| 42 | 0 | Cl | H | H | H | —CF₃ | H | H | H | H | —C(=O)—NH—CH₂CH₃ |
| 43 | 0 | Cl | H | H | H | —CF₃ | H | H | H | H | —C(=O)—OCH₃ |

TABLE I-continued

Structure (I):
Pyridine ring with substituents $R^1, R^2, R^3, R^4$ and N-oxide $(O)_n$, connected via CH(AR) to a phenyl ring with substituents $R^5, R^6, R^7, R^8, R^9$.

| COMP. NO. | n | $R^1$ | $R^2$ | $R^3$ | $R^4$ | $R^5$ | $R^6$ | $R^7$ | $R^8$ | $R^9$ | R |
|---|---|---|---|---|---|---|---|---|---|---|---|
| 44 | 0 | Cl | H | H | H | $-CF_3$ | H | H | H | H | $-C(=O)-O-$phenyl |
| 45 | 0 | Cl | H | H | H | $-CF_3$ | H | H | H | H | $-C(=O)-NH-CH(CH_3)_2$ |
| 46 | 0 | Cl | H | H | H | $-CF_3$ | H | H | H | H | $-C(=O)-NH-CH_2CH_2CH_3$ |
| 47 | 0 | Cl | H | H | H | $-CF_3$ | H | H | H | H | $-C(=O)-CCl_3$ |
| 48 | 0 | Cl | H | H | H | $-CF_3$ | H | H | H | H | $-C(=O)-N(CH_2-CH=CH_2)_2$ |
| 49 | 0 | Cl | H | H | H | $-CF_3$ | H | H | H | H | $-CH(CH_3)-C(=O)-OCH_3$ |
| 50 | DIASTEREOMER OF COMPOUND 49 | | | | | | | | | | |
| 51 | 0 | Cl | H | H | H | $-CF_3$ | H | H | H | H | $-C(=O)-NH-$(3-pyridyl) |
| 52 | 0 | Cl | H | H | H | $-CF_3$ | H | H | H | H | $-C(=O)-N$(2-methylaziridinyl) |
| 53 | 0 | Cl | H | H | H | $-CF_3$ | H | H | H | H | $-C(=O)-N$(thiomorpholinyl) |
| 54 | 0 | Cl | H | H | H | $-CF_3$ | H | H | H | H | $-C(=O)CH_2CH_2CH_3$ |
| 55 | 0 | Cl | H | H | H | $-CF_3$ | H | H | H | H | $-C(=O)-NH-CH_2-C(=O)-OCH_3$ |
| 56 | 0 | Cl | H | H | H | $-CF_3$ | H | H | H | H | $-C(=O)-NH-CH_2-C(=O)-OH$ |
| 57 | 0 | Cl | H | H | H | $-CF_3$ | H | H | H | H | $-CH_2-$phenyl |
| 58 | 0 | Cl | H | H | H | $-CF_3$ | H | H | H | H | $-C(=O)-N(CH_3)(OCH_3)$ |

TABLE I-continued

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 59 | 0 | Cl | H | H | H | —CF₃ | H | H | H | H | $-\overset{\overset{O}{\|}}{C}H$ |
| 60 | 0 | Cl | H | H | H | —CF₃ | H | H | H | H | $-\overset{\overset{O}{\|}}{C}-N(CH_3)(C_2H_5)$ |
| 61 | 0 | Cl | H | H | H | —CF₃ | H | H | H | H | $-\overset{\overset{O}{\|}}{C}-NH-C(CH_3)_3$ |
| 62 | 0 | Cl | H | H | H | —CF₃ | H | H | H | H | $-\overset{\overset{O}{\|}}{C}-N\text{(thiomorpholine S-oxide)}$ |
| 63 | 0 | Cl | H | H | H | —CF₃ | H | H | H | H | $-\overset{\overset{O}{\|}}{C}-N\text{(thiomorpholine S,S-dioxide)}$ |
| 64 | 0 | Cl | H | H | H | —CF₃ | H | H | H | H | $-\overset{\overset{O}{\|}}{C}-NH-\text{(2-pyridyl)}$ |
| 65 | 0 | Cl | H | H | H | —CF₃ | H | H | H | H | $-\overset{\overset{O}{\|}}{C}-NH-CH_2CH_2OCH_3$ |
| 66 | 0 | Cl | H | H | H | —CF₃ | H | H | H | H | $-\overset{\overset{O}{\|}}{C}-N(CH_2CH_2OCH_3)_2$ |
| 67 | 0 | Cl | H | H | H | —CF₃ | H | H | H | H | $-\overset{\overset{O}{\|}}{C}-NH-N(CH_3)_2$ |
| 68 | 0 | Cl | H | H | H | —CF₃ | H | H | H | H | $-\overset{\overset{O}{\|}}{\underset{\overset{\|}{O}}{S}}-N(CH_3)_2$ |
| 69 | 0 | Cl | H | H | H | Cl | —OC₂H₅ | Br | H | H | $-\overset{\overset{O}{\|}}{C}-N(CH_3)_2$ |
| 70 | 0 | Cl | H | H | H | —CH₃ | H | H | H | H | $-\overset{\overset{O}{\|}}{C}-N(CH_3)_2$ |
| 71 | 0 | Br | H | H | H | —CF₃ | H | H | H | H | $-\overset{\overset{O}{\|}}{C}-N(CH_3)_2$ |

TABLE I-continued (I)

[Structure: pyridine ring with R¹, R², R³, R⁴ substituents and N(O)ₙ, connected via CH(AR) to phenyl ring with R⁵, R⁶, R⁷, R⁸, R⁹ substituents]

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 72 | 0 | Cl | H | H | H | —NO₂ | H | CF₃ | H | H | —C(=O)—N(CH₃)₂ |
| 73 | 0 | Cl | H | H | H | Cl | H | H | H | H | —C(=O)—N(CH₃)₂ |
| 74 | 0 | Cl | H | H | H | —CH₃ | H | Cl | H | H | —C(=O)—N(CH₃)₂ |
| 75 | 1 | Cl | H | H | H | —CF₃ | H | H | H | H | —C(=O)—N(CH₃)₂ |
| 76 | 0 | Cl | H | H | H | Br | H | H | H | H | —C(=O)—N(CH₃)₂ |
| 77 | 0 | Cl | H | H | H | Cl | H | H | H | Cl | —C(=O)—N(CH₃)₂ |
| 78 | 0 | Cl | H | H | H | —C₂H₅ | H | H | H | H | —C(=O)—N(CH₃)₂ |
| 70 | 0 | Cl | H | H | H | —NO₂ | H | H | H | H | —C(=O)—N(CH₃)₂ |
| 80 | 0 | Cl | H | H | H | —OCH₃ | H | H | H | H | —C(=O)—N(CH₃)₂ |
| 81 | 0 | Cl | H | H | H | —OCF₃ | H | H | H | H | —C(=O)—N(CH₃)₂ |
| 82 | 0 | Cl | H | H | H | F | H | H | H | H | —C(=O)—N(CH₃)₂ |
| 83 | 0 | Cl | H | H | H | —SC₂H₅ | H | H | H | H | —C(=O)—N(CH₃)₂ |

TABLE I-continued (I)

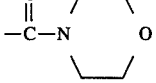

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 84 | 0 | Cl | H | H | H | —CH₃ | H | H | H | H | —C(O)—N(morpholine)O |
| 85 | 0 | Cl | H | H | H | Br | H | H | H | H | —C(O)—N(morpholine)O |
| 86 | 0 | Cl | H | H | H | Cl | H | H | H | Cl | —C(O)—N(morpholine)O |
| 87 | 0 | —CF₃ | H | H | Cl | —CF₃ | H | H | H | H | —C(O)—N(morpholine)O |
| 88 | 0 | Cl | H | H | H | —C₂H₅ | H | H | H | H | —C(O)—N(morpholine)O |
| 89 | 0 | Cl | H | H | H | —OCH₃ | H | H | H | H | —C(O)—N(morpholine)O |
| 90 | 0 | Cl | H | H | H | —SC₂H₅ | H | H | H | H | —C(O)—N(morpholine)O |
| 91 | 0 | Cl | H | H | H | —CH₃ | H | H | H | H | —C(O)—NH—CH₃ |
| 92 | 0 | Cl | H | H | H | Br | H | H | H | H | —C(O)—NH—CH₃ |
| 93 | 0 | Cl | H | H | H | Cl | H | H | H | Cl | —C(O)—NH—CH₃ |
| 94 | 0 | —CF₃ | H | H | Cl | —CF₃ | H | H | H | H | —C(O)—NH—CH₃ |
| 95 | 0 | Cl | H | H | H | —C₂H₅ | H | H | H | H | —C(O)—NH—CH₃ |
| 96 | 0 | Cl | H | H | H | —OCH₃ | H | H | H | H | —C(O)—NH—CH₃ |
| 97 | 0 | Cl | H | H | H | —CH₃ | H | H | H | —CH₃ | —C(O)—NH—CH₃ |
| 98 | 0 | Cl | H | H | H | —OCH₃ | H | H | H | H | —C(O)—NH—C₂H₅ |

TABLE I-continued

(I)

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 99 | 0 | Cl | H | H | H | $-C_2H_5$ | H | H | H | H | $-\overset{O}{\underset{\|}{C}}-NH-C_2H_5$ |
| 100 | 0 | Cl | H | H | H | $-SC_2H_5$ | H | H | H | H | $-\overset{O}{\underset{\|}{C}}-NH-C_2H_5$ |
| 101 | 0 | Cl | H | H | H | $-OCH_3$ | H | H | H | H | $-\overset{O}{\underset{\|}{C}}-C(CH_3)_3$ |
| 102 | 0 | Cl | H | H | H | $-NO_2$ | H | H | H | H | $-\overset{O}{\underset{\|}{C}}-C(CH_3)_3$ |
| 103 | 0 | Cl | H | H | H | $-OCF_3$ | H | H | H | H | $-\overset{O}{\underset{\|}{C}}-C(CH_3)_3$ |
| 104 | 0 | Cl | H | H | H | $-OCH_3$ | H | H | H | H | $-\overset{O}{\underset{\|}{C}}-NH-CH_2CH_2Cl$ |
| 105 | 0 | Cl | H | H | H | $-NO_2$ | H | H | H | H | $-\overset{O}{\underset{\|}{C}}-NH-CH_2CH_2Cl$ |
| 106 | 0 | Cl | H | H | H | $-OCF_3$ | H | H | H | H | $-\overset{O}{\underset{\|}{C}}-NH-CH_2CH_2Cl$ |
| 107 | 0 | Cl | H | H | H | F | H | H | H | H | $-\overset{O}{\underset{\|}{C}}-NH-CH_2CH_2Cl$ |
| 108 | 0 | Cl | H | H | H | $-CH_3$ | H | H | H | H | $-\overset{O}{\underset{\|}{C}}-CH(CH_3)_2$ |
| 109 | 0 | Cl | H | H | H | Br | H | H | H | H | $-\overset{O}{\underset{\|}{C}}-CH(CH_3)_2$ |
| 110 | 0 | Cl | H | H | H | Cl | $-OC_2H_5$ | Br | H | H |  |
| 111 | 0 | Cl | H | H | H | $-NO_2$ | H | $-CF_3$ | H | H |  |
| 112 | 0 | Cl | H | H | H | $-CF_3$ | H | H | H | H | $-\overset{O}{\underset{\|}{C}}-NH-CH_2-CH=CH_2$ |
| 113 | 0 | Cl | H | H | H | $-CF_3$ | H | H | H | H | $-CH_3$ |

TABLE I-continued

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 114 | 0 | Cl | H | H | H | —CF₃ | H | H | H | H | —C(=O)—NH—CH₂—C≡CH |
| 115 | 0 | Cl | H | H | H | —CF₃ | H | H | H | H | —C(=O)—NH—CH₂CH₂CH₂OCH₃ |
| 116 | 0 | Cl | H | H | H | —CF₃ | H | H | H | H | —C(=O)—NH—C(CH₃)₂—C≡CH |
| 117 | 0 | Cl | H | H | H | —CF₃ | H | H | H | H | —C(=O)—C(CH₃)₂—CH₂—CH₂—CH₃ |
| 118 | 0 | Cl | H | H | H | —CF₃ | H | H | H | H | —CH₂CH₃ |
| 119 | 0 | Cl | H | H | H | —CF₃ | H | H | H | H | —CH₂—C(Cl)=CH₂ |
| 120 | 0 | Cl | H | H | H | —CF₃ | H | H | H | H | —C(=O)—NH—CH₂CH₂CH₂—SCH₃ |
| 121 | 0 | Cl | H | H | H | —CF₃ | H | H | H | H | —C(=O)—NH—CH₂CH₂CH₂S(=O)₂CH₃ |
| 122 | 0 | Cl | H | H | H | —CF₃ | H | H | H | H | —C(=O)—NH—CH₂CH₂CH₂S(=O)CH₃ |
| 123 | 0 | Cl | H | H | H | —CF₃ | H | H | H | H | —C(=O)—(4-Cl-C₆H₄) |
| 124 | 0 | Cl | H | H | H | —CF₃ | H | H | H | H | —C(=O)—C₆H₅ |
| 125 | 0 | Cl | H | H | H | —CF₃ | H | H | H | H | —C(=O)—(2-Cl-C₆H₄) |
| 126 | 0 | Cl | H | H | H | —CF₃ | H | H | H | H | —CH₂—C(Cl)=CH |
| 127 | 0 | Cl | H | H | H | —CF₃ | H | H | H | H | —CH₂—C(Cl)(Br)—CH₂ |
| 128 | 0 | Cl | H | H | H | —CF₃ | H | H | H | H | —C(=O)—O—CH₂CH₂OCH₃ |
| 129 | 0 | SCH₃ | H | H | H | —CF₃ | H | H | H | H | —C(=O)—N(CH₃)₂ |
| 130 | 0 | —S(=O)CH₃ | H | H | H | —CF₃ | H | H | H | H | —C(=O)—N(CH₃)₂ |

TABLE I-continued (I)

Structure: pyridine ring with R¹, R², R³, R⁴ substituents, N(O)ₙ, connected via CH(AR) to phenyl ring with R⁵, R⁶, R⁷, R⁸, R⁹.

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 131 | 0 | —S(=O)(=O)—CH₃ | H | H | H | —CF₃ | H | H | H | H | —C(=O)—N(CH₃)₂ |
| 132 | 0 | Cl | H | H | H | Cl | H | H | H | H | —C(=O)—NH—CH₃ |
| 133 | 0 | Cl | H | H | H | Cl | H | H | H | H | —C(=O)—NH—CH₂CH₃ |
| 134 | 0 | Cl | H | H | H | —OCF₃ | H | H | H | H | —C(=O)—NH—CH₂CH₃ |
| 135 | 0 | Cl | H | H | H | —CH₂CH₃ | H | H | H | H | —C(=O)—C(CH₃)₃ |
| 136 | 0 | Cl | H | H | H | Cl | H | H | H | H | —C(=O)—C(CH₃)₃ |
| 137 | 0 | Cl | H | H | H | Br | H | H | H | H | —C(=O)—C(CH₃)₃ |
| 138 | 0 | Cl | H | H | H | CH₃ | H | H | H | H | —C(=O)—C(CH₃)₃ |
| 139 | 0 | Cl | H | H | H | Br | H | H | H | H | —C(=O)—NH—CH₂CH₂—Cl |
| 140 | 0 | Cl | H | H | H | —CH₃ | H | H | H | H | —C(=O)—NH—CH₂—CH₂—Cl |
| 141 | 0 | Cl | H | H | H | —CH₃ | H | H | H | H | —C(=O)—N(CH₂CH₃)₂ |

Compounds where A is —S—

| COMP. NO. | n | R¹ | R² | R³ | R⁴ | R⁵ | R⁶ | R⁷ | R⁸ | R⁹ | R |
|---|---|---|---|---|---|---|---|---|---|---|---|
| 142 | 0 | Cl | H | H | H | —CF₃ | H | H | H | H | —C(=S)—N(CH₂CH₃)₂ |
| 143 | 0 | —OH | H | H | H | —CF₃ | H | H | H | H | —CH₃ |

HERBICIDAL SCREENING TESTS

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

PRE-EMERGENCE HERBICIDAL SCREENING TEST

On the day preceding treatment, seeds of several different weed species were planted in sandy loam soil at a depth of 0.5 inch (1.3 cm) in individual rows using one species per row across the width of a flat. The soil was fortified with 17-17-17 fertilizer (N—P₂O₅—K₂O) on a weight basis and pasteurized. The weeds planted were wild oat (*Avena fatua*) (AVEFA), barnyardgrass (*Echinochloa crusgalli*) (ECHCG), green foxtail (*Setaria viridis*) (SETVI), velvetleaf (*Abutilon theophrasti*) (ABUTH), morningglory species (*Ipomoea* spp.) (IPOSS) and wild mustard (*Sinapsis arvensis*) (SINAR). Plant densities ranged from 3 to 25 plants per row, depending upon the size of the plants.

Solutions of the test compounds were made by weighing out 74.7 or 18.8 milligrams (mg) of the test compound into a 60 ml wide-mouth bottle, then dissolving the compound in 7.0 ml acetone containing 1% Tween 20® (polyoxyethylene sorbitan monolaurate emulsifier) and then adding 7 ml of deionized water to reach a 14 ml final volume. Tween 20® content was 0.5% v/v of the final spray volume. Additional solvents, not exceeding 2 ml, were used if needed to dissolve the compound.

The soil surface was sprayed inside an enclosed linear spray table. The flats were sprayed with the spray solution calibrated to deliver 748 L/ha. The application rate was 4.0 or 1.0 kg/ha.

The flats were placed into a greenhouse at 21°–29° C. and water daily by sprinkling. The degree of weed control was visually assessed and recorded 17–21 days after treatment, as percentage control compared to the growth of the same species of the same age in an untreated check flat.

The results of such pre-emergent testing are summarized in Table II below.

POST-EMERGENCE HERBICIDAL EVALUATION

The soil was prepared and seeded with the same species and methodology described for the pre-emergence test. The flats were placed in the greenhouse at 21°–29° C. and watered by sprinkling. The seeds of the weed species were planted 10–12 days before treatment. In general, grasses were sprayed at a 3 to 4 leaf stage and broadleaves at a 1 to 2 leaf stage. Watering of the treated flats was confined to the soil surface and not to the foliage of the germinated plants. The degree of weed control was visually assessed and recorded 17–21 days after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that a test was not performed at that level of application.

The results are listed in Table III below.

TABLE II

| COMP. NO. | Pre-Emergent - Testing (4.0 kg/ha) | | | | | |
|---|---|---|---|---|---|---|
| | AVEFA | ECHCG | SETVI | ABUTH | IPOSS | SINAR |
| 1 | 0 | 0 | —* | 0 | 0 | 0 |
| 2 | 0 | 0 | —* | 0 | 0 | 0 |
| 3 | 0 | 0 | 0 | 0 | 0 | 0 |
| 4 | 10 | 98 | 10 | 30 | 30 | 10 |
| 5 | 0 | 0 | 0 | 0 | 0 | 0 |
| 6 | 0 | 0 | 0 | 0 | 0 | 0 |
| 7 | 0 | 98 | 15 | 70 | 20 | 25 |
| 8 | 0 | 0 | 0 | 0 | 0 | 0 |
| 9 | 0 | 0 | 0 | 0 | 0 | 0 |
| 10 | 5 | 50 | 10 | 5 | 10 | 0 |
| 11 | 0 | 0 | 0 | 0 | 10 | 0 |
| 12 | 0 | 10 | 10 | 0 | 10 | 0 |
| 13 | 0 | 10 | 10 | 0 | 10 | 0 |
| 14 | 5 | 100 | 20 | 40 | 40 | 25 |
| 15 | 40 | 95 | 15 | 60 | 20 | 30 |
| 16 | 30 | 5 | 100 | 0 | 0 | 0 |
| 17 | 10 | 98 | 10 | 60 | 60 | 15 |
| 18 | 0 | 0 | 0 | 0 | 0 | 0 |
| 19 | 15 | 90 | 90 | 0 | 0 | 0 |
| 20 | 0 | 98 | 0 | 10 | 10 | 20 |
| 21 | 20 | 100 | 10 | 40 | 10 | 20 |
| 22 | 50 | 98 | 40 | 60 | 10 | 40 |
| 23 | 5 | 0 | 70 | 10 | 0 | 0 |
| 24 | 10 | 98 | 100 | 90 | 80 | 50 |
| 25 | 0 | 25 | 95 | 70 | 10 | 60 |
| 26 | 5 | 98 | 20 | 70 | 50 | 0 |
| 27 | 20 | 100 | 100 | 98 | 95 | 75 |
| 28 | 5 | 98 | 10 | 60 | 0 | 10 |
| 29 | 5 | 98 | 80 | 70 | 5 | 15 |
| 30 | 5 | 100 | 20 | 70 | 20 | 20 |
| 31 | 95 | 100 | 100 | 98 | 95 | 90 |
| 32 | 95 | 100 | 100 | 100 | 98 | 85 |
| 33 | 5 | 100 | 100 | 85 | 90 | 20 |
| 34 | 10 | 25 | 100 | 75 | 5 | 10 |
| 35 | 60 | 100 | 80 | 85 | 95 | 25 |
| 36 | 25 | 100 | 95 | 30 | 60 | 20 |
| 37 | 98 | 100 | 100 | 98 | 95 | 80 |
| 38 | 60 | 100 | 100 | 90 | 95 | 70 |
| 39 | 98 | 100 | 100 | 95 | 95 | 90 |

TABLE II-continued

Pre-Emergent - Testing (4.0 kg/ha)

| COMP. NO. | AVEFA | ECHCG | SETVI | ABUTH | IPOSS | SINAR |
|---|---|---|---|---|---|---|
| 40 | 0 | 90 | 95 | 60 | 80 | 5 |
| 41 | 98 | 100 | 100 | 98 | 95 | 60 |
| 42 | 98 | 100 | 100 | 100 | 95 | 90 |
| 43 | 50 | 100 | 30 | —* | 15 | 30 |
| 44 | 5 | 100 | 20 | 60 | 20 | 10 |
| 45 | 98 | 100 | 100 | 100 | 95 | 70 |
| 46 | 98 | 100 | 100 | 100 | 95 | 85 |
| 47 | 75 | 100 | 100 | 70 | 85 | 75 |
| 48 | 15 | 100 | 100 | 60 | 90 | 50 |
| 49 | 0 | 10 | 100 | 40 | 10 | 15 |
| 50 | 0 | 0 | 10 | 5 | 5 | 10 |
| 51 | 0 | 10 | 100 | 0 | 0 | 10 |
| 52 | 98 | 100 | 100 | 98 | 95 | 80 |
| 53 | 98 | 100 | 100 | 70 | 90 | 40 |
| 54 | 20 | 100 | 30 | 50 | 20 | 60 |
| 55 | 0 | 0 | 0 | 0 | 5 | 0 |
| 56 | 0 | 0 | 0 | 5 | 5 | 10 |
| 57 | 60 | 100 | 100 | 95 | 100 | 85 |
| 58 | 40 | 100 | 100 | 70 | 100 | 40 |
| 59 | 10 | 100 | 100 | 70 | 5 | 10 |
| 60 | 95 | 100 | 100 | 100 | 95 | 75 |
| 61 | 40 | 100 | 100 | 5 | 10 | 0 |
| 62 | 95 | 100 | 100 | 70 | 95 | 40 |
| 63 | 90 | 100 | 100 | 60 | 95 | 60 |
| 64 | 0 | 0 | 0 | 0 | 0 | 0 |
| 65 | 98 | 100 | 100 | 98 | 95 | 75 |
| 66 | 10 | 100 | 100 | 60 | 90 | 30 |
| 67 | 98 | 100 | 100 | 90 | 90 | 75 |
| 68 | 60 | 100 | 60 | 80 | 30 | 70 |
| 69 | 5 | 70 | 25 | 5 | 10 | 30 |
| 70 | 85 | 100 | 100 | 90 | 95 | 60 |
| 71 | 0 | 0 | 0 | 0 | 0 | 0 |
| 72 | 0 | 10 | 10 | 5 | 0 | 0 |
| 73 | 70 | 100 | 100 | 90 | 90 | 40 |
| 74 | 5 | 95 | 90 | 10 | 10 | 0 |
| 75 | 80 | 100 | 100 | 60 | 80 | 10 |
| 76 | 25 | 100 | 100 | 100 | 95 | 30 |
| 77 | 5 | 100 | 100 | 60 | 50 | 15 |
| 78 | 95 | 100 | 100 | 90 | 100 | 85 |
| 79 | 25 | 100 | 100 | 100 | 0 | 25 |
| 80 | 25 | 100 | 100 | 50 | 90 | 5 |
| 81 | 90 | 100 | 100 | 95 | 95 | 60 |
| 82 | 40 | 100 | 100 | 70 | 85 | 5 |
| 83 | 0 | 100 | 98 | 60 | 90 | 20 |
| 84 | 70 | 100 | 100 | 90 | 98 | 60 |
| 85 | 60 | 100 | 100 | 100 | 95 | 90 |
| 86 | 20 | 100 | 100 | 100 | 95 | 25 |
| 87 | 0 | 5 | 0 | 5 | 10 | 0 |
| 88 | 98 | 100 | 100 | 100 | 95 | 60 |
| 89 | 90 | 100 | 100 | 90 | 100 | 60 |
| 90 | 30 | 100 | 98 | 70 | 90 | 10 |
| 91 | 98 | 100 | 100 | 70 | 90 | 50 |
| 92 | 98 | 100 | 100 | 100 | 98 | 75 |
| 93 | 70 | 100 | 100 | 15 | 90 | 15 |
| 94 | 0 | 10 | 0 | 0 | 0 | 0 |
| 95 | 100 | 100 | 100 | 100 | 98 | 100 |
| 96 | 98 | 100 | 100 | 75 | 95 | 50 |
| 97 | 95 | 100 | 100 | 30 | 98 | 15 |
| 98 | 85 | 100 | 100 | 80 | 95 | 50 |
| 99 | 98 | 100 | 100 | 90 | 95 | 85 |
| 100 | 40 | 100 | 98 | 50 | 40 | 20 |
| 101 | 15 | 100 | 100 | 0 | 15 | 5 |
| 102 | 0 | 100 | 100 | 0 | 0 | 0 |
| 103 | 75 | 100 | 100 | 60 | 90 | 20 |
| 104 | 85 | 100 | 100 | 60 | 95 | 20 |
| 105 | 85 | 100 | 100 | 30 | 30 | 30 |
| 106 | 100 | 100 | 100 | 100 | 95 | 70 |
| 107 | 50 | 100 | 100 | 25 | 85 | 10 |
| 108 | 5 | 15 | 20 | 5 | 5 | 10 |
| 109 | 10 | 10 | 20 | 0 | 5 | 40 |
| 110 | 0 | 0 | 40 | 0 | 0 | 0 |
| 111 | 0 | 0 | 0 | 0 | 0 | 0 |
| 112 | 95 | 100 | 100 | 90 | 95 | 85 |
| 113 | 10 | 85 | 100 | 10 | 5 | 10 |
| 114 | 75 | 100 | 100 | 90 | 90 | 50 |

TABLE II-continued

Pre-Emergent - Testing (4.0 kg/ha)

| COMP. NO. | AVEFA | ECHCG | SETVI | ABUTH | IPOSS | SINAR |
|---|---|---|---|---|---|---|
| 115 | 80 | 100 | 100 | 90 | 90 | 60 |
| 116 | 5 | 100 | 100 | 85 | 90 | 60 |
| 117 | 50 | 100 | 100 | 95 | 90 | 80 |
| 118 | 20 | 100 | 100 | 10 | 15 | 5 |
| 119 | 10 | 100 | 100 | 75 | 90 | 60 |
| 120 | 10 | 100 | 95 | 10 | 0 | 20 |
| 121 | 0 | 60 | 100 | 20 | 10 | 10 |
| 122 | 0 | 70 | 98 | 10 | 0 | 20 |
| 123 | 5 | 100 | 100 | 50 | 10 | 30 |
| 124 | 30 | 100 | 100 | 70 | 50 | 60 |
| 125 | 20 | 100 | 100 | 85 | 90 | 80 |
| 126 | 5 | 10 | 60 | 0 | 0 | 10 |
| 127 | 20 | 100 | 100 | 60 | 5 | 90 |
| 128 | 15 | 100 | 100 | 75 | 80 | 60 |
| 129 | 10 | 30 | 98 | 0 | 5 | 30 |
| 130 | 25 | 70 | 98 | 30 | 30 | 10 |
| 131 | 10 | 95 | 98 | 50 | 75 | 20 |
| 132 | 90 | 100 | 100 | 70 | 95 | 60 |
| 133 | 95 | 100 | 100 | 85 | 95 | 50 |
| 134 | 90 | 100 | 100 | 90 | 90 | 90 |
| 135 | 70 | 100 | 100 | 90 | 95 | 80 |
| 136 | 25 | 100 | 100 | 50 | 90 | 50 |
| 137 | 30 | 100 | 100 | 70 | 90 | 50 |
| 138 | 30 | 100 | 100 | 90 | 90 | 90 |
| 139 | 80 | 100 | 100 | 80 | 90 | 30 |
| 140 | 90 | 100 | 100 | 50 | 80 | 75 |
| 141 | 25 | 100 | 100 | 90 | 98 | 90 |
| 142 | 0 | 10 | 60 | 0 | 40 | 10 |
| 143 | 15 | 20 | 80 | 15 | 0 | 10 |

\* — indicates not tested

TABLE III

Post-Emergent - Testing (4.0 kg/ha)

| COMP. NO. | AVEFA | ECHCG | SETVI | ABUTH | IPOSS | SINAR |
|---|---|---|---|---|---|---|
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 70 | 20 | 0 | 10 | 0 |
| 5 | 0 | 0 | 0 | 0 | 0 | 0 |
| 6 | 0 | 0 | 0 | 0 | 0 | 0 |
| 7 | 0 | 95 | 20 | 5 | 30 | 5 |
| 8 | 0 | 0 | 0 | 0 | 5 | 15 |
| 9 | 0 | 0 | 0 | 0 | 5 | 0 |
| 10 | 0 | 0 | 0 | 0 | 20 | 10 |
| 11 | 5 | 10 | 10 | 0 | 0 | 0 |
| 12 | 0 | 0 | 10 | 0 | 5 | 0 |
| 13 | 0 | 0 | 10 | 0 | 5 | 0 |
| 14 | 10 | 70 | 30 | 5 | 80 | 10 |
| 15 | 0 | 0 | 0 | 5 | 15 | 0 |
| 16 | 0 | 0 | 0 | 0 | 5 | 0 |
| 17 | 5 | 5 | 15 | 10 | 15 | 10 |
| 18 | 0 | 0 | 0 | 0 | 0 | 0 |
| 19 | 0 | 0 | 0 | 0 | 10 | 0 |
| 20 | 0 | 0 | 0 | 0 | 15 | 5 |
| 21 | 0 | 25 | 5 | 15 | 10 | 0 |
| 22 | 10 | 90 | 15 | 5 | 90 | 5 |
| 23 | 5 | 0 | 70 | 10 | 0 | 0 |
| 24 | 5 | 0 | 25 | 100 | 85 | 75 |
| 25 | 0 | 0 | 0 | 85 | 85 | 20 |
| 26 | 10 | 95 | 5 | 10 | 60 | 0 |
| 27 | 85 | 98 | 85 | 100 | 95 | 85 |
| 28 | 10 | 95 | 5 | 0 | 20 | 0 |
| 29 | 10 | 98 | 10 | 5 | 30 | 0 |
| 30 | 0 | 98 | 5 | 90 | 90 | 0 |
| 31 | 90 | 98 | 90 | 95 | 90 | 80 |
| 32 | 15 | 95 | 85 | 90 | 90 | 80 |
| 33 | 5 | 80 | 85 | 95 | 90 | 60 |
| 34 | 15 | 10 | 25 | 85 | 60 | 15 |
| 35 | 10 | 98 | 60 | 98 | 90 | 40 |
| 36 | 10 | 70 | 50 | 80 | 90 | 75 |

TABLE III-continued

Post-Emergent - Testing (4.0 kg/ha)

| COMP. NO. | AVEFA | ECHCG | SETVI | ABUTH | IPOSS | SINAR |
|---|---|---|---|---|---|---|
| 37 | 95 | 98 | 90 | 98 | 90 | 85 |
| 38 | 5 | 98 | 40 | 98 | 90 | 75 |
| 39 | 90 | 98 | 85 | 100 | 90 | 85 |
| 40 | 25 | 30 | 30 | 95 | 90 | 60 |
| 41 | 90 | 98 | 90 | 98 | 90 | 90 |
| 42 | 90 | 95 | 90 | 90 | 90 | 90 |
| 43 | 20 | 95 | 20 | 30 | 30 | 5 |
| 44 | 0 | 50 | 20 | 60 | 60 | 10 |
| 45 | 90 | 100 | 90 | 95 | 90 | 85 |
| 46 | 90 | 98 | 90 | 95 | 90 | 75 |
| 47 | 5 | 98 | 60 | 10 | 20 | 70 |
| 48 | 15 | 100 | 80 | 98 | 95 | 80 |
| 49 | 5 | 10 | 15 | 60 | 60 | 30 |
| 50 | 0 | 0 | 20 | 10 | 15 | 0 |
| 51 | 0 | 0 | 20 | 60 | 80 | 15 |
| 52 | 95 | 100 | 98 | 95 | 90 | 75 |
| 53 | 60 | 100 | 90 | 95 | 90 | 60 |
| 54 | 75 | 100 | 30 | 75 | 85 | 10 |
| 55 | 0 | 10 | 0 | 20 | 20 | 70 |
| 56 | 0 | 0 | 0 | 5 | 25 | 15 |
| 57 | 20 | 98 | 95 | 95 | 95 | 95 |
| 58 | 60 | 100 | 98 | 98 | 90 | 80 |
| 59 | 5 | 98 | 20 | 10 | 15 | 5 |
| 60 | 75 | 100 | 98 | 100 | 90 | 80 |
| 61 | 15 | 40 | 30 | 30 | 85 | 15 |
| 62 | 70 | 95 | 95 | 98 | 90 | 50 |
| 63 | 85 | 98 | 95 | 50 | 85 | 60 |
| 64 | 0 | 0 | 0 | 0 | 5 | 5 |
| 65 | 95 | 100 | 95 | 98 | 95 | 60 |
| 66 | 15 | 20 | 40 | 80 | 90 | 75 |
| 67 | 60 | 98 | 85 | 85 | 90 | 50 |
| 68 | 10 | 98 | 15 | 30 | 10 | 20 |
| 69 | 0 | 0 | 0 | 75 | 90 | 75 |
| 70 | 70 | 98 | 90 | 95 | 90 | 70 |
| 71 | 0 | 0 | 0 | 0 | 0 | 0 |
| 72 | 0 | 5 | 15 | 30 | 10 | 10 |
| 73 | 5 | 95 | 90 | 95 | 90 | 40 |
| 74 | 5 | 25 | 10 | 75 | 20 | 20 |
| 75 | 10 | 40 | 60 | 98 | 90 | 70 |
| 76 | 90 | 98 | 90 | 95 | 90 | 90 |
| 77 | 10 | 50 | 70 | 80 | 75 | 80 |
| 78 | 90 | 100 | 95 | 95 | 85 | 75 |
| 79 | 15 | 100 | 85 | 80 | 85 | 30 |
| 80 | 30 | 95 | 85 | 85 | 90 | 25 |
| 81 | 95 | 98 | 90 | 100 | 90 | 40 |
| 82 | 5 | 95 | 90 | 60 | 90 | 75 |
| 83 | 5 | 70 | 85 | 95 | 90 | 60 |
| 84 | 85 | 95 | 75 | 80 | 90 | 60 |
| 85 | 50 | 95 | 75 | 50 | 80 | 30 |
| 86 | 30 | 100 | 70 | 60 | 85 | 30 |
| 87 | 0 | 0 | 0 | 0 | 5 | 0 |
| 88 | 90 | 98 | 90 | 95 | 90 | 80 |
| 89 | 90 | 98 | 90 | 90 | 85 | 50 |
| 90 | 15 | 95 | 60 | 95 | 90 | 25 |
| 91 | 90 | 95 | 80 | 90 | 90 | 60 |
| 92 | 95 | 100 | 90 | 95 | 90 | 75 |
| 93 | 40 | 40 | 15 | 30 | 60 | 50 |
| 94 | 0 | 0 | 0 | 0 | 0 | 0 |
| 95 | 90 | 98 | 90 | 98 | 90 | 70 |
| 96 | 95 | 98 | 98 | 98 | 85 | 40 |
| 97 | 90 | 98 | 95 | 60 | 85 | 15 |
| 98 | 100 | 100 | 100 | 98 | 85 | 60 |
| 99 | 98 | 100 | 100 | 98 | 90 | 95 |
| 100 | 25 | 95 | 75 | 90 | 90 | 20 |
| 101 | 60 | 75 | 30 | 75 | 85 | 75 |
| 102 | 10 | 100 | 85 | 70 | 90 | 20 |
| 103 | 50 | 100 | 95 | 90 | 95 | 60 |
| 104 | 98 | 100 | 98 | 90 | 80 | 50 |
| 105 | 60 | 100 | 85 | 50 | 20 | 10 |
| 106 | 90 | 98 | 95 | 100 | 90 | 60 |
| 107 | 40 | 85 | 90 | 30 | 95 | 20 |
| 108 | 20 | 20 | 30 | 60 | 60 | 40 |
| 109 | 5 | 25 | 15 | 60 | 75 | 80 |
| 110 | 0 | 0 | 0 | 25 | 25 | 15 |
| 111 | 0 | 0 | 0 | 10 | 10 | 0 |

TABLE III-continued

| | Post-Emergent - Testing (4.0 kg/ha) | | | | | |
|---|---|---|---|---|---|---|
| COMP. NO. | AVEFA | ECHCG | SETVI | ABUTH | IPOSS | SINAR |
| 112 | 90 | 95 | 90 | 98 | 90 | 80 |
| 113 | 0 | 0 | 10 | 15 | 20 | 0 |
| 114 | 80 | 98 | 90 | 98 | 90 | 70 |
| 115 | 85 | 98 | 90 | 90 | 90 | 60 |
| 116 | 70 | 98 | 85 | 70 | 90 | 30 |
| 117 | 5 | 95 | 90 | 98 | 95 | 85 |
| 118 | 10 | 10 | 20 | 20 | 80 | 15 |
| 119 | 5 | 98 | 85 | 90 | 90 | 80 |
| 120 | 0 | 10 | 50 | 50 | 90 | 85 |
| 121 | 0 | 0 | 30 | 70 | 85 | 15 |
| 122 | 0 | 5 | 20 | 80 | 90 | 60 |
| 123 | 0 | 5 | 10 | 95 | 75 | 75 |
| 124 | 20 | 98 | 30 | 90 | 70 | 80 |
| 125 | 10 | 50 | 80 | 95 | 90 | 25 |
| 126 | 5 | 20 | 60 | 90 | 90 | 85 |
| 127 | 15 | 25 | 60 | 70 | 95 | 80 |
| 128 | 25 | 90 | 60 | 75 | 95 | 80 |
| 129 | 0 | 10 | 20 | 60 | 85 | 30 |
| 130 | 10 | 40 | 85 | 98 | 90 | 10 |
| 131 | 5 | 60 | 85 | 90 | 90 | 10 |
| 132 | 95 | 100 | 95 | 85 | 90 | 90 |
| 133 | 90 | 98 | 90 | 85 | 85 | 80 |
| 134 | 90 | 98 | 90 | 98 | 90 | 90 |
| 135 | 50 | 95 | 90 | 95 | 90 | 90 |
| 136 | 20 | 98 | 85 | 75 | 90 | 50 |
| 137 | 15 | 95 | 90 | 90 | 90 | 70 |
| 138 | 20 | 98 | 90 | 90 | 95 | 70 |
| 139 | 90 | 98 | 90 | 95 | 90 | 70 |
| 140 | 75 | 98 | 90 | 75 | 85 | 60 |
| 141 | 10 | 60 | 60 | 60 | 60 | 80 |
| 142 | 0 | 0 | 10 | 60 | 90 | 50 |
| 143 | 0 | 5 | 10 | 30 | 60 | 5 |

The results above illustrate the preemergent and postemergent efficacy of the present compounds against a variety of grasses and broadleaf species.

What is claimed is:

1. An herbicidal composition comprising:

(A) a compound of the formula:

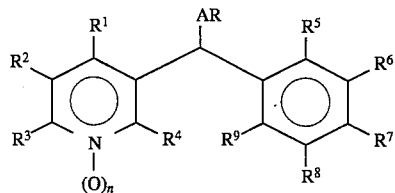

wherein:

$R^1$ and $R^5$ are each independently halogen, $C_1$–$C_6$ haloalkyl, $C_1$–$C_6$ alkyl, $C_1$–$C_6$ alkoxy, $C_1$–$C_6$ haloalkoxy, ($C_1$–$C_6$)alkoxy-($C_1$–$C_6$)alkyl, —S(O)$_m$—$R^{10}$, cyano, —OH, thiocyano, nitro or —N($R^{11}$)($R^{12}$);

$R^2$, $R^3$ and $R^4$ are each independently hydrogen, $C_1$–$C_6$ alkyl, nitro, halogen, $C_1$–$C_6$ alkoxy, $C_1$–$C_6$ haloalkoxy, $C_1$–$C_6$ haloalkyl or —S(O)$_m$—$R^{10}$;

$R^6$, $R^7$, and $R^8$ are each independently hydrogen, halogen, $C_1$–$C_6$ alkyl, $C_2$–$C_6$ alkenyl, $C_2$–$C_6$ alkynyl, nitro, —N($R^{11}$)($R^{12}$), $C_1$–$C_6$ haloalkyl, $C_1$–$C_6$ alkoxy $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, cyano, —C(X)—$R^{10}$ or —S(O)$_m$—$R^{10}$;

$R^9$ is hydrogen, halogen, $C_1$–$C_6$ alkyl, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, —S(O)$_m$—$R^{10}$, cyano, hydroxy, thiocyano, nitro or —N($R^{11}$)($R^{12}$);

A is oxygen or sulfur;

n is 0 or 1;

R is hydrogen, hydrocarbyl, hydrocarbyl substituted with one or more of halogen or $C_1$–$C_6$ alkoxy or is of the formula —C(X)—$R^{10}$, —C(O)—C(O)—$R^{10}$, —S(O)$_2$—$R^{10}$ or —P(X)($R^{15}$)($R^{16}$);

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula —N($R^{11}$)($R^{12}$);

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl; hydroxycarbonyl($C_1$–$C_6$)alkyl; or N($R^{13}$)($R^{14}$) wherein $R^{13}$ and $R^{14}$ are each independently hydrogen, $C_1$–$C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1$–$C_6$ alkyl;

$R^{15}$ and $R^{16}$ are each independently $C_1$–$C_6$ alkyl, $C_1$–$C_6$ alkylthio or $C_1$–$C_6$ alkoxy; and m is 0, 1 or 2;

or an agriculturally acceptable salts thereof;

(B) a co-herbicide selected from the group consisting of anilide herbicides, triketone and cyclohexanedione herbicides, imidazolidinone herbicides, sulfonylurea herbicides and phenoxyphenoxypropionate herbicides; and (C) a carrier therefor.

2. A composition in accordance with claim 1 wherein $R^1$ is halogen.

3. A composition in accordance with claim 2 wherein $R^1$ is chloro or bromo.

4. A composition in accordance with claim 2 wherein $R^2$, $R^3$ and $R^4$ are hydrogen.

5. A composition in accordance with claim 1 wherein $R^5$ is halogen, $C_1$–$C_6$ alkyl, $C_1$–$C_6$ haloalkyl, $C_1$–$C_6$ haloalkoxy, $C_1$–$C_6$ alkoxy, nitro, or —S(O)$_m$alkyl wherein m is 0, 1 or 2.

6. A composition in accordance with claim 5 wherein $R^6$, $R^7$, $R^8$ and $R^9$ are each independently hydrogen, $C_1$–$C_6$ alkyl, halogen or $C_1$–$C_6$ alkoxy.

7. A composition in accordance with claim 1 wherein R is phenyl-($C_1$–$C_3$)alkyl or is of the formula

wherein $R^{12}$ is $C_1$–$C_{12}$ alkyl, $C_1$–$C_6$ haloalkyl, phenyl or is of the formula

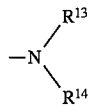

wherein $R^{13}$ and $R^{14}$ are each independently $C_1$–$C_{12}$ alkyl, hydrogen, $C_2$–$C_{12}$ alkenyl, $C_2$–$C_{12}$ alkynyl, phenyl, $C_1$–$C_{12}$ haloalkyl, $C_1$–$C_6$ alkoxy, ($C_1$–$C_6$)alkoxy($C_1$–$C_6$)alkyl or $R^{13}$ and $R^{14}$ together with the ring to which they are bound form a morpholine, piperidine or pyrrolidine ring.

8. A composition in accordance with claim 7 wherein R is benzyl or is of the formula

wherein $R^{12}$ is $C_1$–$C_6$ alkyl or is of the formula

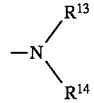

wherein $R^{13}$ and $R^{14}$ are each independently hydrogen, phenyl, $C_1$–$C_6$ haloalkyl or $C_1$–$C_6$ alkyl or together $R^{13}$ and $R^{14}$ form a morpholine ring.

9. A composition in accordance with claim 1 wherein:

$R^1$ is halogen;

$R^2$, $R^3$ and $R^4$ are hydrogen;

$R^5$ is halogen, $C_1$–$C_6$ alkyl, $C_1$–$C_6$ haloalkyl, $C_1$–$C_6$ haloalkoxy, $C_1$–$C_6$ alkoxy, nitro or —S(O)$_m$($C_1$–$C_3$)alkyl wherein m is 0, 1 or 2;

$R^6$, $R^7$, $R^8$ and $R^9$ are each independently hydrogen, $C_1$–$C_6$ alkyl, halogen or $C_1$–$C_6$ alkoxy; and R is phenyl-($C_1$–$C_3$)alkyl or is of the formula

wherein $R^{12}$ is $C_1$–$C_{12}$ alkyl, $C_1$–$C_6$ haloalkyl, phenyl or is of the formula

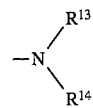

wherein $R^{13}$ and $R^{14}$ are each independently $C_1$–$C_{12}$ alkyl, hydrogen, $C_2$–$C_{12}$ alkenyl, phenyl, $C_2$–$C_{12}$ alkynyl, $C_1$–$C_{12}$ haloalkyl, $C_1$–$C_6$ alkoxy, ($C_1$–$C_6$)alkoxy($C_1$–$C_6$)alkyl or $R^{13}$ and $R^{14}$ together with the nitrogen to which they are bound form a morpholine, piperidine or pyrrolidine ring.

10. A composition in accordance with claim 1 wherein:

$R^1$ is chloro or bromo;

$R^5$ is trifluoromethyl, trifluoromethoxy, chloro, bromo, methoxy, methyl or ethyl;

$R^2$, $R^3$, $R^4$, $R^7$ and $R^8$ are hydrogen;

$R^6$ and $R^9$ are each independently hydrogen, chloro or methyl; and

R is benzyl or is of the formula

wherein $R^{12}$ is $C_1$–$C_6$ alkyl or is of the formula

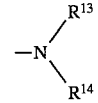

wherein $R^{13}$ and $R^{14}$ are independently hydrogen, phenyl, $C_1$–$C_6$ haloalkyl or $C_1$–$C_6$ alkyl or together $R^{13}$ and $R^{14}$ form a morpholine ring.

11. A composition according to claim 1, wherein said co-herbicide is selected from the group consisting of metolachlor, imazaquin, bensulfuron and the methyl ester thereof, chlorosulfuron and dichlofop.

12. A method for controlling undesirable vegetation comprising applying to the area where control is desired an herbicidally effective amount of a an herbicidal composition comprising:

(A) a compound of the formula:

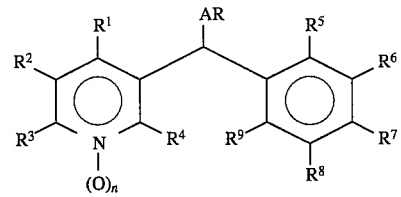

wherein:

$R^1$ and $R^5$ are each independently halogen, $C_1$–$C_6$ haloalkyl, $C_1$–$C_6$ alkyl, $C_1$–$C_6$ alkoxy, $C_1$–$C_6$ haloalkoxy, ($C_1$–$C_6$)alkoxy-($C_1$–$C_6$)alkyl, —S(O)$_m$—$R^{10}$, cyano, —OH, thiocyano, nitro or —N($R^{11}$)($R^{12}$);

$R^2$, $R^3$ and $R^4$ are each independently hydrogen, $C_1$–$C_6$ alkyl, nitro, halogen, $C_1$–$C_6$ alkoxy, $C_1$–$C_6$ haloalkoxy, $C_1$–$C_6$ haloalkyl or —S(O)$_m$—$R^{10}$;

$R^6$, $R^7$, and $R^8$ are each independently hydrogen, halogen, $C_1$–$C_6$ alkyl, $C_2$–$C_6$ alkenyl, $C_2$–$C_6$ alkynyl, nitro, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, cyano, —C(X)—$R^{10}$ or —S(O)$_m$—$R^{10}$;

$R^9$ is hydrogen, halogen, $C_1$–$C_6$ alkyl, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, —S(O)$_m$—$R^{10}$, cyano, hydroxy, thiocyano, nitro or —N($R^{11}$)($R^{12}$);

A is oxygen or sulfur;

n is 0 or 1;

R is hydrogen, hydrocarbyl, hydrocarbyl substituted with one or more of halogen or $C_1$–$C_6$ alkoxy or is of the formula —C(X)—$R^{10}$, —C(O)—C(O)—$R^{10}$, —S(O)$_2$—$R^{10}$ or —P(X)($R^{15}$)($R^{16}$);

wherein:

X is O or S;

$R^{10}$ is hydrocarbyl, substituted hydrocarbyl, hydrocarbyloxy, substituted hydrocarbyloxy, hydrocarbyl-S—, substituted hydrocarbyl-S— or is of the formula —N($R^{11}$)($R^{12}$);

wherein $R^{11}$ and $R^{12}$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^{13}$)($R^{14}$) wherein $R^{13}$ and $R^{14}$ are each independently hydrogen, $C_1$–$C_6$ alkyl or phenyl;

or $R^{11}$ and $R^{12}$ together with the nitrogen to which they are bound form an aziridine, piperazine, morpholine, thiomorpholine, thiomorpholine sulfinyl, thiomorpholine sulfonyl, hexamethyleneimine, piperidine or pyrrolidine ring, any of which may be optionally substituted with $C_1$–$C_6$ alkyl;

$R^{15}$ and $R^{16}$ are each independently $C_1$–$C_6$ alkyl, $C_1$–$C_6$ alkylthio or $C_1$–$C_6$ alkoxy; and m is 0, 1 or 2;

or an agriculturally acceptable salt thereof;

(B) a co-herbicide selected from the group consisting of anilide herbicides, triketone and cyclohexanedione herbicides, imidazolidinone herbicides, sulfonylurea herbicides and phenoxyphenoxypropionate herbicides; and (C) a carrier therefor.

13. A method according to claim 12, wherein said co-herbicide is selected from the group consisting of metolachlor, imazaquin, bensulfuron and the methyl ester thereof, chlorosulfuron and dichlofop.

* * * * *